(12) United States Patent
Sugiyama et al.

(10) Patent No.: US 6,225,051 B1
(45) Date of Patent: *May 1, 2001

(54) METHOD OF DETECTING SOLID CANCER CELLS AND TISSUE ATYPIA AND METHOD OF TESTING TISSUES FOR USE IN BONE MARROW TRANSPLANTATION AND PERIPHERAL BLOOD STEM CELL TRANSPLANTATION

(75) Inventors: Haruo Sugiyama, 2-19-30, Senbanishi, Mino-shi, Osaka 562; Kazushi Inoue, Ibaraki, both of (JP)

(73) Assignees: Haruo Sugiyama; Tadamitsu Kishimoto, both of Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/973,967

(22) PCT Filed: Apr. 15, 1997

(86) PCT No.: PCT/JP97/01300

§ 371 Date: Jun. 26, 1998

§ 102(e) Date: Jun. 26, 1998

(87) PCT Pub. No.: WO97/39354

PCT Pub. Date: Oct. 23, 1997

(30) Foreign Application Priority Data

Apr. 16, 1996 (JP) .................................... 8-094050
Apr. 16, 1996 (JP) .................................... 8-094051
Apr. 17, 1996 (JP) .................................... 8-095427

(51) Int. Cl.$^7$ .................................... C12Q 1/68
(52) U.S. Cl. .................................... 435/6; 435/41.1
(58) Field of Search ........................................ 435/6, 91.1

(56) References Cited

U.S. PATENT DOCUMENTS 5,622,835    4/1997    Herlyn .

FOREIGN PATENT DOCUMENTS

95/29995    11/1995    (WO) .

OTHER PUBLICATIONS

Inoue et al, *Process of Medical Science*, 175(13):934–340 (1995) (with English Translation thereof).
Call et al, *Cell*, 60:509–520 (1993).
Pelletier et al, *Genes and Development*, 5:1345–1356 (1991).
Buckler et al, *Molecular and Cellular Biology*, 11(3):1707–1712 (1991).
Amin et al, *Amer. J. Path.*146(2):344–356 (1995).
Silberstein et al, *Proc. Natl. Sci. USA*, 94:8132–8137 (1997).
Tilly et al, *Endocrinology*, 136(4):1394–1402 (1995).
Bruening et al, *Cancer Investigation*, 11(4):393–399 (1993).
Gerald et al, *Amer. J. of Pathol.*, 140 (5):1031–1037 (1992).
Inoue et al, *Blood*, 84(9):3071–3079 (1994).

*Primary Examiner*—James Ketter
(74) *Attorney, Agent, or Firm*—Sughrue, Mion, Zinn, Macpeak & Seas, PLLC

(57) ABSTRACT

The invention provides a method of detecting solid cancer cells which comprises determining the level of expression of WT1 gene in a test tissue, a method of detecting the atypia of a tissue which comprises determining the level of expression of WT1 gene in the tissue, and a method of testing a graft material tissue for bone marrow or peripheral blood stem cell transplantation which comprises determining the level of expression of WT1 gene in a CD34$^-$ cell fraction of the tissue to detect leukemic cells and solid cancer cells in the tissue.

7 Claims, 3 Drawing Sheets

F I G. 2
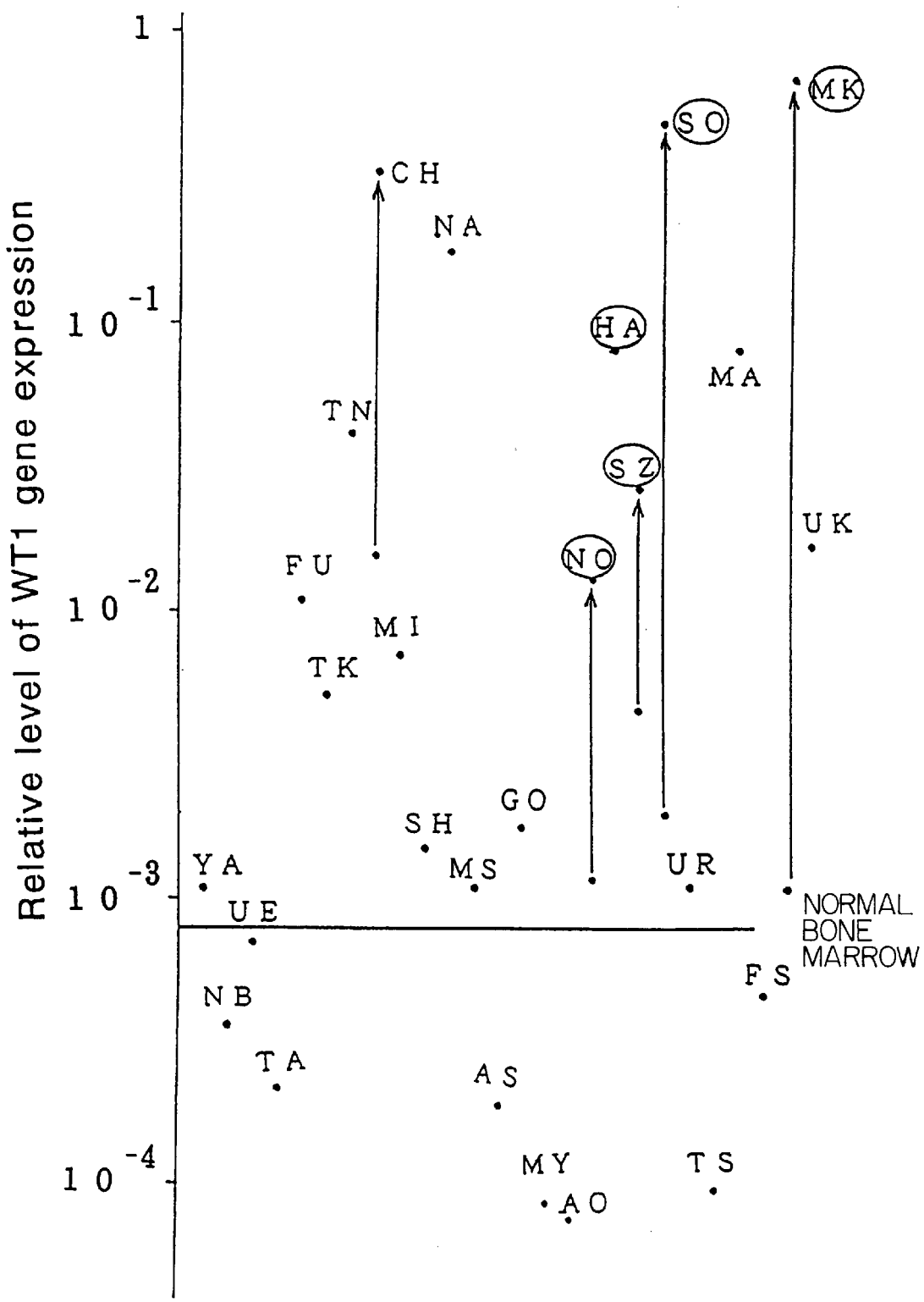

METHOD OF DETECTING SOLID CANCER CELLS AND TISSUE ATYPIA AND METHOD OF TESTING TISSUES FOR USE IN BONE MARROW TRANSPLANTATION AND PERIPHERAL BLOOD STEM CELL TRANSPLANTATION

TECHNICAL FIELD

The present invention relates to a method of detecting solid cancer cells and tissue atypia and to a method of testing tissues for use in bone marrow transplantation or peripheral blood stem cell transplantation. More particularly, the present invention relates to a novel technology which is not only useful for the diagnosis and detection of solid cancers and detection of atypia such as myelodysplastic syndrome and the like but also instrumental in assessment of the safety of cells for use in allogenic bone marrow transplantation or autologous hematopoietic stem cell transplantation in patients with leukemia or a solid cancer, particularly assessment of the risk of recurrence after transplantation.

BACKGROUND ART

The WT1 gene was isolated from human chromosome 11p13 as one of the genes etiologically associated with Wilms' tumor on the basis of an analysis of WAGR syndrome involving such complications as Wilms' tumor, aniridia, urogenital anomalies, mental retardation, etc. It is known that its expression is substantially confined to the fetal kidney, spleen, testis, and ovary [Molecular Medicine, Vol. 32, No. 5, p. 502 (1995)].

The inventors of the present invention reported previously that the level of WT1 gene expression is high in acute leukemia, that this level of expression is inversely correlated with prognosis, and that the so-called MRD (minimal residual disease) in acute leukemia can be detected by determining said expression level [Blood, Vol. 84, No. 9, p. 3071 (1994)].

The expression level of the WT1 gene can be determined by the well-known reverse transcribed polymerase chain reaction (RT-PCR; Kawasaki, E. S. et al., Amplification of RNA, in PCR Protocol, A Guide to Methods and Applications, Academic Press, Inc., San Diego, 21–27 (1991)) and this determination has proved clinically significant as far as leukemia is concerned.

On the other hand, a solid cancer is a neoplastic condition in which cancer cells grow in a solid mass and is quite distinct from leukemia in which tumor cells severally grow, infiltrate, and metastasize.

Heretofore, much research has been undertaken into solid cancers but no clinical marker corresponding to said WT1 gene in leukemia has been reported as yet.

Meanwhile, myelodysplastic syndrome (MDS) is an acquired hematopoietic disturbance featuring preleukemia and a refractory decrease in peripheral blood cell count. Its definite diagnosis depends on detection of a morphological abnormality of blood cells and, here, disease typing has so far been made according to the FAB (French-American-British Group) classification.

It is known that MDS mentioned above progresses to acute leukemia at a high rate and the incidence of leukemic transformation is said to be not less than 40% in the high-risk group and as high as 10–15% even in the low-risk group.

With regard to the prognosis and prognostic factors for MDS, the above-mentioned FAB classification is well known and the risks for acute leukemia are said to be high blast ratios of bone marrow and peripheral blood, clusters of blasts on bone marrow biopsy, and complicated chromosomal aberrations [Naika Gaku (Internal Medicine), p. 1711, Sep. 25, 1995, Asakura Shoten].

As diseases which may undergo leukemic transformation in the similar way, myelofibrosis, polycythemia vera, aplastic anemia, primary thrombocytosis, and paroxysmal nocturnal hemoglobinuria, among others, are known but there has not been available an established technology for detecting MDS and other diseases progressing to leukemia, i.e. an atypia with morphological features distinct from those of the normal tissue or cells.

Meanwhile, in patients with leukemia, a therapeutic modality which comprises performing an allogenic bone marrow transplantation (alloBMT), i.e. transfusion of hematopoietic stem cells, for avoiding irreversible hematopoietic disorders and concurrently instituting an anticancer drug therapy, a radiation therapy, and/or the like for exterminating leukemic cells in cooperation with the immune reactions of the patient and thereby achieving a complete cure has been practiced with some success. More recently, peripheral blood stem cell transplantation (PBSCT) or autologous BSCT (ABSCT), in lieu of autologous bone marrow transplantation (ABMT) which is a kind of said bone marrow transplantation, has been adopted by clinicians with increasing avidity because of its numerous advantages.

In such a bone marrow or peripheral blood stem cell transplantation, the myelocytes or peripheral blood stem cells from a donor with a substantially or completely compatible HLA antigen are transplanted into the patient. The hematopoietic stem cells in the graft then start normal hematopoiesis enlisting the help of the interstitial cells and hematopoietic factors in the bone marrow, thus leading to a recovery of hematopoiesis. While such a bone marrow or peripheral blood stem cell transplantation is rewarded with a fair success, the practice involves the grave problem of recurrence after transplantation in addition to the scarcity of donors and the graft-related complications.

To overcome the above-mentioned recurrence and other problems, it is most essential to insure that the very tissue or cells to be transplanted are free of cancer cells such as leukemic cells, that is to say the safety of the donor's bone marrow or peripheral blood stem cells, but there has not been available an established technology for testing whether leukemic cells are included among myelocytes or peripheral blood stem cells.

It is, therefore, an object of the present invention to provide a technology for quantitating tumor cells which is of value for the diagnosis of solid cancers, more particularly a quantitative test utilizing a clinical marker correlated with solid cancers.

Another object of the present invention is to provide a technology for detecting atypia utilizing a novel marker by which the risk of acute leukemic transformation, for instance, can be predicted with greater accuracy taking into consideration the course and prognosis of MDS in particular.

It is a still another object of the present invention to provide a novel technology which permits detection of leukemic cells in the tissue for use in said bone marrow transplantation or peripheral blood stem cell transplantation.

DISCLOSURE OF THE INVENTION

As the result of their intensive research directed to the above-mentioned objects, the inventors of the present invention discovered for the first time that the WT1 gene, which is a well-known clinical marker of leukemia, shows a significantly high level of expression in solid cancers which are unrelated to leukemia. Accordingly they found that this gene can be effectively utilized in the detection of solid cancer cells.

The inventors further found that the level of WT1 gene expression is also high in MDS and other variants which are clearly differentiated from leukemia and that the expression level of the WT1 gene in such a variant can be an indicator of acute leukemic transformation.

Furthermore, the inventors of the present invention found that although the expression level of the WT1 gene in the CD34$^+$ cell fraction of a graft material cannot be an indicator of contamination with leukemic cells, the level of WT1 gene expression in the CD34$^-$ cell fraction can be a good marker of contamination with leukemic cells and solid cancer cells and that determination of this level enables the detection of leukemic cells and solid cancer cells. The present invention has been developed on the basis of the above findings.

The present invention provides a method for detecting cancer cells which comprises determining the level of expression of the WT1 gene in a tissue to be tested to thereby detect solid cancer cells.

The present invention also provides a method for detecting the atypia of a tissue to be tested which comprises determining the level of expression of the WT1 gene in said tissue.

Particularly, this method for detection of atypia is preferably applied when the tissue to be tested is one presenting with myelodysplastic syndrome (preleukemia) or when the determination of the expression level of the WT1 gene is made on its transcript.

The term "atypia" is used herein to mean a morphological variation from the normal tissue or cell and its degree is generally parallel to the malignancy of a tumor [Saishin Igaku Dai-Jiten (Contemporary and Comprehensive Medical Encyclopedia), Jun. 15, 1987, Ishiyaku Shuppan].

The method for detecting atypia according to the invention is essentially predicated on the use of the level of WT1 gene expression as a test for atypia, that is to say the use of said expression level as an indicator of acute leukemic transformation in MDS and other diseases mentioned above. As such, the method has a great clinical significance for assessment of the prognosis or course of such diseases inclusive of MDS.

The method for detecting atypia according to the invention has the following additional clinical significance. Thus, taking a patient with MDS as an example, when the WT1 value determined by the method of the invention increases gradually from a low level, it can be considered that the patient has a high risk for acute leukemia, thus indicating an early allogehic bone marrow transplantation or allogenic peripheral blood stem cell transplantation.

Furthermore, the method for detecting atypia according to the invention can be used for diagnosing whether atypical cells have emerged in blood in healthy humans, victims of radiation hazards (the personnel employed in an atomic power plant, workers handling radiations, patients on radiation therapy, etc.), persons who received anticancer therapy for breast cancer, and patients presenting with leukemoid symptoms induced by infections.

In addition, the present invention provides a method for testing a tissue for use as a graft material in bone marrow transplantation or peripheral blood stem cell transplantation, which comprises determining the level of WT1 expression in the CD34$^-$ cell fraction of a graft material for transplantation to thereby detect leukemic cells and solid cancer cells in said material.

The abbreviations used for amino acids, peptides, nucleotide or base sequences, and nucleic acids in this specification are conforming to those adopted by IUPAC-IUB or the "Guideline for the Drafting of Specifications Including Base Sequences or Amino Acid Sequences" (edited by the Japanese Patent Office) and those in routine use in the art.

The WT1 gene which is determined by the technology of the present invention is known as such and its base sequence is shown in the literature [e.g. Cell, 60, 509 (1990); Nature, 343, 774 (1990)].

What counts in the technology of the invention is to determine the expression level of said WT1 gene in a test tissue or a CD34$^-$ cell fraction thereof and this is the most outstanding feature shared by the various methods disclosed herein.

Meanwhile, the technology for determining the expression level of genes in general is known as, for example, can be seen from the literature cited above and there is no limitation on the procedures or protocols which can be used for determination of the expression level of said particular gene in accordance with the present invention. Thus, not only the RT-PCR method described in the above literature but also other known techniques or protocols can be successfully employed.

The expression level of the WT1 gene can be specifically determined by, for example, the technique for detecting a transcript of the WT1 gene in the test tissue or the technique for detecting a translation product thereof. According to the former technique, the mRNA as a transcript of the WT1 gene is detected to determine the expression level of the same gene and this detection can be made successfully by said RT-PCR, Northern blot analysis [Molecular Cloning, Cold Spring Harbor Laboratory (1989)], in situ RT-PCR [Nucleic Acids Res., 21, 3159–3166 (1993)] and in situ hybridization, which are determinations at the cellular level, NASBA method [Nucleic acid sequence-based amplification, Nature, 350, 91–92 (1991)], and other methods.

According to the latter technique, the WT1 protein which is a translation product of the WT1 gene is detected to determine the expression level of said gene and this methodology can be implemented by, for example, an immunological assay using a specific antibody against the WT1 protein. The specific antibody against the WT1 protein can be produced as necessary by using the WT1 protein as an immunogen in the routine manner [Leukemia, 9, 1060 (1995)].

There is no particular limitation on the test sample that can be used only if it contains a transcript or translation product of the WT1 gene. For determination of the transcript, various tissue components inclusive of tissue cells derived from peripheral blood, lymph node, bone marrow fluid, pleural fluid, ascites, cerebrospinal fluid, surgical washes, isolated tissues, hair, and other tissues can be employed. For determination of the translation product, not only the tissue components mentioned above but also various body fluids from which they are derived can be used.

The results of determination on the transcript or translation product of the WT1 gene in such samples are correlated with the levels of WT1 gene expression in the corresponding test tissues, thus enabling the necessary determination of the expression level of the WT1 gene.

When the level of WT1 gene expression is higher than that in normal cells or healthy humans, the cells, tissue, or subject in question can be regarded as solid tumor cells or a tissue or subject harboring them, or as being atypical or those containing atypia. In this manner, solid cancer cells and atypia can be detected in accordance with the present invention. Therefore, the technology of the invention is not only of great value in the clinical examination and diagnosis of solid cancers but, by enabling a positive monitoring of leukemic transformation in patients, proves of great value in the clinical examination and diagnosis of atypia.

The embodiment of the technology for detecting solid cancer cells and atypia in accordance with the invention through determination of a transcript of the WT1 gene is now described in detail.

As already mentioned in reference to the prior art, the inventors of the present invention reported on the detection of leukemic cells by determination of the level of WT1 gene expression [Blood, Vol. 84, No. 9, p. 3071 (1994)]. The methods described there for determining the level of WT1 gene expression by RT-PCR and Northern blot analysis, respectively, can both be utilized with success in the detection according to the present invention. The detailed protocols are described in the above literature and are hereby incorporated in this specification by reference.

Now, the RNA of the sample can be extracted, purified, and prepared in the conventional manner. When the detection of a transcript of the WT1 gene as contained in this RNA is to be carried out by Northern blotting, there is no limitation on the detection probe that can be used only if it contains the WT1 gene or a fragment thereof and has a sufficient specificity to permit detection under the detecting conditions used in the procedure of hybridization with the test RNA sample. Thus, the probe includes the WT1 gene, fragments available upon cleavage with restriction enzymes, and oligonucleotides chemically synthesized according to the base sequence of the WT1 gene.

When RT-PCR is used, the primers used need not be critical in amplification region or base length, all that is necessary being capable of amplifying the WT1 gene alone. It is preferably so designed that they contain the whole zinc finger domain of the WT1 gene, and generally the primer may have a partial sequence of about 15–30 nucleotides. Such a primer set can be established in the routine manner and a preferred example is shown in the example presented hereinafter.

The various procedures which can be employed in the detection technology of the present invention, such as chemical synthesis of a partial gene, enzymatic treatments for cleavage, deletion, addition or ligation thereof, and the isolation, purification, replication, and selection of them can all be performed in the conventional manner [e.g. Bunshi Idengaku Jikken Ho (Experimental Protocols in Molecular Genetics), Kyoritsu Shuppan, 1983; PCR Technology, Takara Shuzo, 1990].

By way of illustration, the above-mentioned isolation and purification can be carried out by agarose gel electrophoresis, and base sequencing can be made by, for example, the dideoxy method [Proc. Natl. Acad. Sci., U.S.A., 74, 5463–5467 (1977)], the Maxam-Gilbert method [Method in Enzymology, 65, 499–560 (1980)], or the like. The latter can be easily carried out using a commercial sequencing kit. PCR can also be carried out under the routine conditions [e.g. Science, 230, 1350–1354 (1985)]. Those basic protocols are used in the various reports referred to in this specification as well and, together with the example given hereinafter, can be consulted as references.

In carrying out the detection technology of the present invention, it is advantageous to use a solid cancer and atypia detection kit containing suitable reagents for determining the expression level of the WT1 gene as active ingredients.

The detection kit should contain specific reagents tailored to the specific method of determining the expression level of the WT1 gene as essential components. Such specific reagents are appropriately chosen and established according to the particular detection protocol adopted and are defined as reagents necessary for the means for specific detection of the target according to the invention, such as anti-WT1 protein antibody, WT1 gene transcript detection probe, and/or the corresponding primer set, among others. Furthermore, although not considered to be essential components of such a detection kit, reagents for PCR may also be included in the kit just like the reagents for hybridization, for instance. The present invention, thus, provides a kit for the detection of solid cancer cells and atypia and a kit for cancer diagnosis.

The method for testing tissues for bone marrow transplantation or peripheral blood stem cell transplantation is now described in detail. This test method comprises determining the level of WT1 expression in a $CD34^-$ cell fraction available upon elimination of $CD34^+$ cells from a graft material.

This determination of the expression level of the WT1 gene can be carried out by using a variety of techniques just as mentioned for the method for detecting solid cancer cells and atypia which has been described hereinbefore.

The sample that can be used for this test is the $CD34^-$ cell fraction available upon elimination of CD34+ cells from any tissue for use as a graft material by a well-known suitable technique. As examples, such fractions of peripheral blood stem cells, bone marrow fluid, etc. can be mentioned. Such a $CD34^-$ cell fraction can be isolated by the routine procedure, typically column chromatography using a CD34 column or a substance having an affinity for CD34 cells, such as FACS, or a magnetic cell separator. The column that can be typically used for this procedure includes Ceparate (manufactured by Cell-Pro), Isolex 300 and 50 (Baxter), and MaCS (Amzene), among others.

The separation procedure using a magnetic cell separator is now described in detail. First, the mobilized peripheral blood available upon elimination of platelets etc. by centrifugation or the like or the bone marrow fluid available upon elimination of mononuclear cells by means of a Ficoll pack or the like and subsequent centrifugation is reacted with anti-CD34 monoclonal antibody for sensitization and, then, reacted with Dynabeads to which a secondary antibody has been conjugated to cause resetting. This rosette (positive cell-antibody-Dynabead complex) is magnetically separated from non-rosetting cells (negative cells). From the rosette thus obtained, positive cells can be harvested by enzymatic treatment with chymopapain.

It has been found that this method of determining the level of WT1 gene expression in the above sample, that is a transcript or translation product of the WT1 gene, provides a value well correlated with the available number of leukemic cells or solid cancer cells and that when this measured value is not over the $10^{-4}$ level, the sample can be assessed to contain substantially no leukemic or solid cancer cells. Therefore, in accordance with this invention, the presence of leukemic cells and solid cancer cells in a graft material for transplantation can be tested and, hence, the safety of the graft material can be assured.

In the above test for graft materials in accordance with the invention, reagents similar to those already mentioned for the detection-diagnostic kit for solid cancer cells and atypia

BRIEF DESCRIPTION OF THE DRAWINGS

FIG. 2 is a diagrammatic representation of the plots obtained by determining the level of WT1 gene expression in various patients in accordance with Example 2.

BEST MODE FOR PRACTICING THE INVENTION

Figure 1:
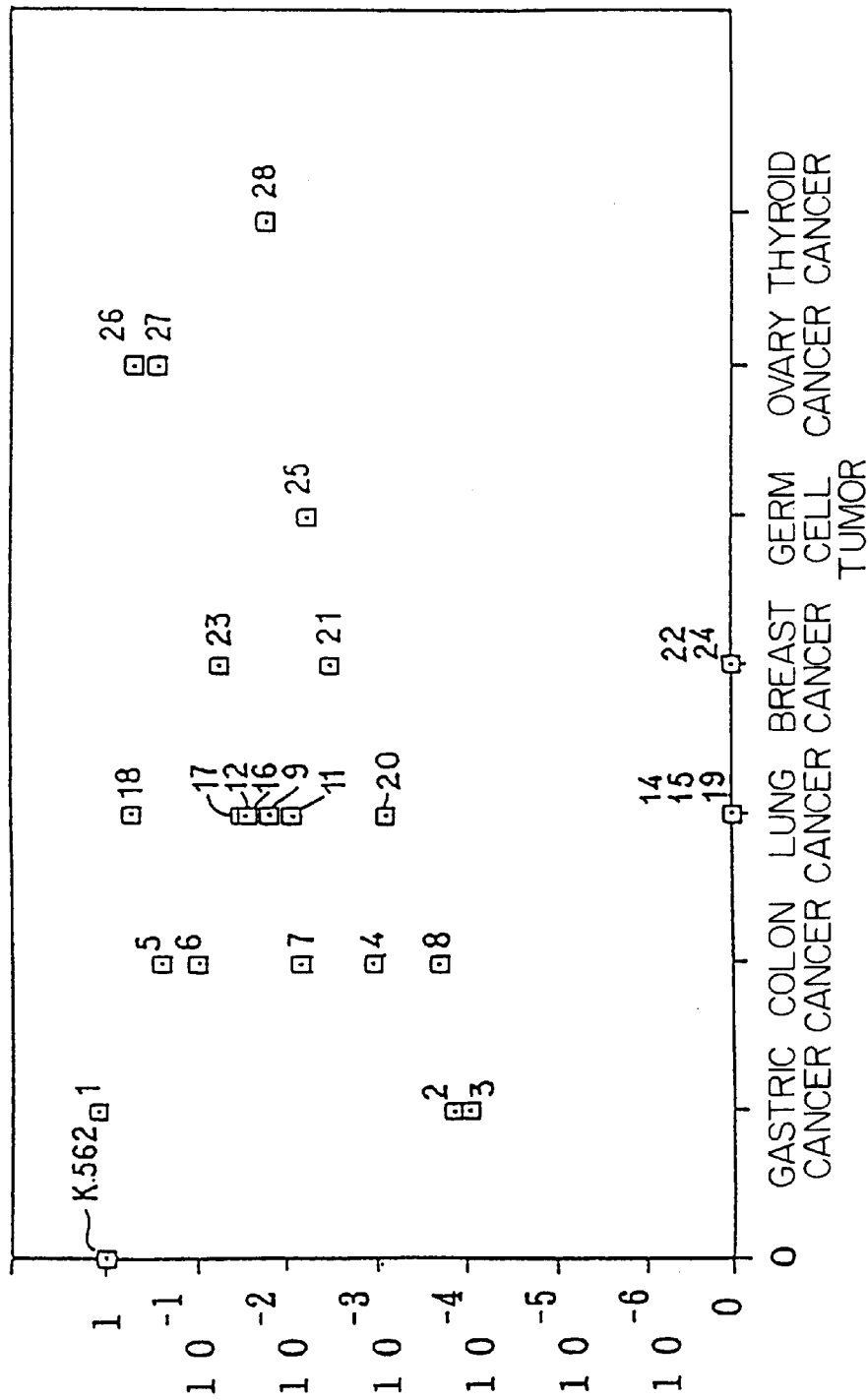
FIG. 1 is a diagrammatic representation of the data generated by determining the level of WT1 gene expression in various cancer cells in accordance with Example 1.

The following examples are further illustrative of the present invention in detail.

EXAMPLE 1

Detection of solid cancer cells

As solid cancer cells, the following cell lines derived from various tissues were used. The JCRB number of each cell line is one assigned by Japanese Cancer Research Bank (JCRB).

Gastric cancer
(1) AZ-521 . . . Gastric cancer (JCRB0061)
(2) MKN1 . . . Gastric cancer, adenosquamous carcinoma (JCRB0252)
(3) MKN28 . . . Gastric cancer (JCRB0253)

Colon cancer
(4) LOVO . . . Colon adenocarcinoma (Cancer Res., 36, 467–475 (1976))
(5) SW480 . . . Colon adenocarcinoma (Cancer Res., 38, 3186–3190 (1978))
(6) SW620 . . . Colon adenocarcinoma (Laboratory Investigation, 44, 309–323 (1981))
(7) COLO0320DM . . . Colon adenocarcinoma (Anticancer Res., 13, 2011–2019 (1993))
(8) HT29 . . . Colon adenocarcinoma (Clinical Molecular Pathology, 48, M326–M332 (1995))

Lung cancer
(9) OS1 . . . Lung cancer, Small cell carcinoma (Japanese J. Cancer Res., 81, 289–297 (1990))
(11) OS2R . . . Lung cancer, Small cell carcinoma (Cancer Res., 56, 354–358 (1996))
(12) OS3 . . . Lung cancer, Small cell carcinoma (Japanese J. Cancer Res., 81, 289–297 (1990))
(14) LU65A . . . Lung cancer, small cell carcinoma (JCRB0054)
(15) LU65B . . . Lung cancer, small cell carcinoma (JCRB0055)
(16) LU99B . . . Lung cancer, giant cell carcinoma (JCRB0057)
(17) LU99C . . . Lung cancer, giant cell carcinoma (JCRB0058)
(18) VMRC-LCP . . . Lung cancer, squamous cell carcinoma (JCRB0103)
(19) LC6 . . . Lung cancer, Small cell carcinoma
(20) RERF-LC-MS . . . Lung cancer, adenocarcinoma (JCRB0081)

Breast cancer
(21) MDA MB231 . . . Breast cancer (Endocrinology, 129, 323–329 (1991))
(22) ZR75 . . . Breast cancer (Mol. Cell Endocr., 41, 197–204 (1985))
(23) YMB1 . . . Breast cancer (JCRB0823)
(24) T47D . . . Breast cancer (Endocrinology, 129, 323–329 (1991))

Germ cell tumor
(25) NEC8 . . . Germ cell tumor (testis) (JCRB0250)

Ovarian cancer
(26) TYK NU . . . Ovary cancer, undifferentiated (JCRB0234.0)
(27) TYK-nu. cp-r . . . Ovary cancer, undifferenciated (JCBR0234. 1)

Thyroid cancer
(28) Cancer cells from patients with cancer of the thyroid

The expression level of the WT1 gene in those cell lines were determined in accordance with the protocol described in the literature [Blood, 84(9), 3071 (1994)], as follows.

Thus, total RNA was extracted from each cell line by the routine method [e.g. acid-guanidine-phenol-chloroform method; Anal. Biochem., 162, 156 (1987)], dissolved in diethyl pyrocarbonate-treated water, and quantitated optically at 260 nm.

Thus, 15.5 µl of diethyl pyrocarbonate-treated water containing 1 µg of total RNA was heated at 65° C. for 5 minutes and mixed with 14.5 µl of RT buffer (50 mmol/l Tris-Hcl (ph 8.3), 70 mmol/l KCl, 3 mmol/l $MgCl_2$, 10 mmol/l dithiothreitol) containing 600 U reverse transcriptase (Moloney murine leukemia virus reverse transcriptase, GIBCO-BRL), 500 mmol/l each deoxynucleotide triphosphate (dNTP, Pharmacia), 750 ng oligo dT primer set, and 40 U RNase inhibitor (Boehringer Mannheim).

This mixture was incubated at 37° C. for 90 minutes, heated at 70° C. for 20 minutes, and stored at −20° C. until use.

PCR was performed on a DNA thermal cycler (Perkin Elmer-Cetus) in a round of cycles of denaturation at 94° C.×1 min., primer annealing at 64° C.×1 min. (β actin: 60° C.×1 min.), and chain elongation at 72° C.×2 min. to provide a PCR product (first round PCR).

When the densitometer unit (described below) of this PCR product was less than 500, a second round PCR with the nested inner primer set was carried out using a 2.5 µl aliquot of the first round PCR product.

The PCR product thus obtained was assayed in accordance with the protocol given-in the literature [J. Immunol., 147, 4307 (1991)], as follows.

Thus, the PCR product from 20 ng of total RNA was cloned on 1.3% agarose gel containing 0.05 µg/ml of ethidium bromide and photographed using polaroid film (Polaroid 665 film, Polaroid Corp.).

The negative film was developed at 25° C. for 5 minutes and scanned with a densitomer (CS-9000, Shimadzu) to find the "densitomer unit".

The result for the PCR product obtained in the absence of RNA under otherwise the same conditions was used as negative control.

The primers used in the above procedures are shown in Table 1.

TABLE 1

| First round PCR primers | Base sequences |
| --- | --- |
| Outer sense primer | 5'-GGCATCTGAGACCAGTGAGAA-3' (SEQ ID No:1) |
| Outer antisense primer | 5'-GAGAGTCAGACTTGAAAGCAGT-3' (SEQ ID No:2) |
| Second round PCR primer | Base sequences |
| Inner sense primer | 5'-GCTGTCCCACTTACAGATGCA-3' (SEQ ID No:3) |
| Inner antisense primer | 5'-TCAAAGCGCCAGCTGGAGTTT-3' (SEQ ID No:4) |

As the primers for β actin used as an internal control, those described in the literature [Proc. Natl. Acad. Sci. USA., 82, 6133, (1985)] were used. The respective primers were invariably synthesized by the conventional chemical method.

To standardize the amount of RNA for RT-PCR and the difference in RNA decomposition of samples, the result (densitomer unit) with the WT1 gene was divided by the result with β actin and the value was used as the level of WT1 expression.

Furthermore, with the level of WT1 gene expression in the cell line K562 known to have the WT1 gene expressed [Lozzio, C. B. and Lozzio, B. B., Human chronic myelogenous leukemia cell line with positive Philadelphia chromosome, Blood, 45, 321–334 (1995)] as determined by the above procedure being taken as the reference (1.00), the levels of WT1 gene expression in various test cells were calculated as relative ratios.

The results are presented in FIG. 1.

In FIG. 1, the ordinate represents the relative ratios of WT1 gene expression in various cell lines with the level of WT1 gene expression in the cell line K562 (K562 in the table) being taken as 1.00, while the abscissa represents test cells (gastric cancer, colon cancer, lung cancer, breast cancer, germ cell tumor, ovary cancer, and thyroid cancer cells, represented by the numbers assigned hereinbefore).

It is apparent from FIG. 1 that WT1 has been highly expressed in all the gastric cancer, colon cancer, lung cancer, breast cancer, germ cell tumor, ovary cancer, and thyroid cancer cells, indicating that WT1 can be used as a tumor marker for such solid cancer cells. It is accordingly clear that a clinically valuable, novel detection and assay technology for solid cancers has been established.

(pH 8.3), 70 mmol/l KCl, 3 mmol/l $MgCl_2$, 10 mmol/l dithiothreitol) containing 600 U reverse transcriptase (Moloney murine leukemia virus reverse transcriptase, GIBCO-BRL), 500 mmol/l each deoxynucleotide triphosphate (dNTP, Pharmacia), 750 ng oligo dT primer set, and 40 U RNase inhibitor (Boehringer Mannheim). This mixture was incubated at 37° C. for 90 minutes, heated at 70° C. for 20 minutes, and stored at −20° C. until use.

PCR was performed on a DNA thermal cycler (Perkin Elmer-Cetus) in a round of cycles of denaturation at 94° C.×1 min., primer annealing at 64° C.×1 min. (β actin: 60° C.×1 min.), and chain elongation at 72° C.×2 min. to provide a PCR product (first round PCR).

When the densitometer unit (described below) of this PCR product was less than 500, a second round PCR with the nested inner primer set was carried out using a 2.5 μl aliquot of the first round PCR product.

The PCR product thus obtained was assayed in accordance with the protocol given in the literature [J. Immunol., 147, 4307 (1991)], as follows.

Thus, the PCR product from 20 ng of total RNA was cloned on 1.3% agarose gel containing 0.05 μg/ml of ethidium bromide and photographed using polaroid film (Polaroid 665 film, Polaroid Corp.). The negative film was developed at 25° C. for 5 minutes and scanned with a densitomer (CS-9000, Shimadzu) to find the "densitomer unit". The result for the PCR product obtained in the absence of RNA under otherwise the same conditions was used as negative control.

The primers used in the above procedures are shown in Table 2.

TABLE 2

| First round PCR primers | Base sequences |
| --- | --- |
| Outer sense primer | 5'-GGCATCTGAGACCAGTGAGAA-3' (SEQ ID NO:5) |
| Outer antisense primer | 5'-GAGAGTCAGACTTGAAAGCAGT-3' (SEQ ID NO:6) |
| Second round PCR primer | Base sequences |
| Inner sense primer | 5'-GCTGTCCCACTTACAGATGCA-3' (SEQ ID NO:7) |
| Inner antisense primer | 5'-TCAAAGCGCCAGCTGGAGTTT-3' (SEQ ID NO:8) |

EXAMPLE 2

Detection of MDS (1) Determination of the level of WT1 gene expression

The level of WT1 gene expression was determined in accordance with the protocol described in the literature [Blood, 84(9): 3071, 1994], as follows.

Thus, total RNA was extracted from each sample by the routine method [acid-guanidine-phenol-chloroform method, Anal. Biochem., 162, 156 (1987)], dissolved in diethyl pyrocarbonate-treated water, and quantitated optically at 260 nm.

Thus, 15.5 μl of diethyl pyrocarbonate-treated water containing 1 μg of total RNA was heated at 65° C. for 5 minutes and mixed with 14.5 μl of RT buffer (50 mmol/l Tris-HCl As the primers for β actin used as an internal control, those described in the literature [Proc. Natl. Acad. Sci. USA., 82, 6133, (1985)] were used. The respective primers were invariably synthesized by the conventional chemical method.

To standardize the amount of RNA for RT-PCR and the difference in RNA decomposition of samples, the result (densitomer unit) with the WT1 gene was divided by the result with β actin and the value was used as the level of WT1 gene expression. Furthermore, with the level of WT1 gene expression in the cell line K562 known to have the WT1 gene expressed [Lozzio, C. B. and Lozzio, B. B., Human chronic myelogenous leukemia cell line with positive Philadelphia chromosome, Blood, 45, 321–334 (1995)]

as determined by the above procedure being taken as the reference 1.00, the levels of WT1 gene expression in various samples were calculated as relative ratios.

From 18 MDS patients (TA, UE, FU, TK, TN, CH, NA, MI, SH, AO, NO, SZ, HA, SO, UR, MK, UK, and TS), 2 myelofibrosis patients (MY and MA), 1 leukocytosis patient (NB), 1 patient with aplastic anemia (YA), 1 patient with polycythemia vera (AS), 1 eosinophilia patient (MS), and 2 patients with primary thrombocytosis (GO and FS), or a total of 26 patients, bone marrow and peripheral blood were sampled and the level of WT1 gene expression in each sample was determined by the procedure described above. The results are shown in FIG. 2.

Plotted (on the abscissa) in FIG. 2 are the relative values of the level of WT1 gene expression in each sample with the level of WT1 gene expression in the K562 line being taken as 1.00.

The relative level of WT1 gene expression in the normal bone marrow ($8.0 \times 10^{-4}$) is shown as a reference line on the abscissa. The encircled patients, in the diagram, died subsequently.

As regards 5 MDS patients (CH, NO, SZ, SO, and MK), the levels of WT1 gene expression found by the redetermination performed 3 months (CH), 1 year (NO), 6 months (SZ), 3 months (SO), and 2 months (MK), respectively, after the initial determination are indicated by the arrow.

The following can be understood from FIG. 2.

Thus, the MDS patients NO (after 1 year), SZ (after 6 months), and SO (after 3 months), who had invariably shown high measured values in the initial determination, became progressively atypical in a short period of time and ultimately died of leukemic transformation.

On the other hand, the MDS patients TA, AO, and TS showed low levels of WT1 gene expression and remained clinically stable, thus being cases of a low risk of leukemic transformation.

Thus, in accordance with the technology of the invention, not only the detection of atypia is made feasible but the risk of leukemic transformation in MDS patients can be predicted by serial determination of the level of WT1 gene expression.

EXAMPLE 3

Testing graft materials

As graft materials for peripheral blood stem cell transplantation, peripheral blood stem cells were isolated from various patients to whom granulocyte colony stimulating factor (G-CSF; "Gran", product of Kirin-Sankyo, or "Neutrogin", prosuct of Chugain) had been administered ahead of time (autologous peripheral blood stem cell transplantation: 2 μg/kg body weight×3~7 days; allogenic peripheral blood stem cell transplantation: 10 μg/kg body weight×7 days) had been administered ahead of time. From the isolated peripheral blood stem cells, CD34⁻ cells were separated and recovered using a cell separation system (Isolex 50, product of Baxter) [e.g. J. Hematotherapy, 4, 531–438 (1995)].

This procedure was carried out in accordance with the manufacturer's manual. The cells were first reacted with anti-CD34 monoclonal antibody and then reacted with Dynabeads conjugated with a secondary antibody for rosetting. This rosette (positive cell-antibody-Dynabeads complex) is separated from non-resetting cells (negative cells). From this rosette, positive cells can be recovered by enzymatic treatment with chymopapain.

The expression level of the WT1 gene in the CD34⁻ fractions from said patients were determined in accordance with the protocol described in the literature [Blood, 84(9), 3071 (1994)], as follows.

Thus, total RNA was extracted from each fraction by the routine method [e.g. acid-guanidine-phenol-chloroform method; Anal. Biochem., 162, 156 (1987)], dissolved in diethyl pyrocarbonate-treated water, and quantitated optically at 260 nm.

Thus, 15.5 μl of diethyl pyrocarbonate-treated water containing 1 μg of total RNA was heated at 65° C. for 5 minutes and mixed with 14.5 μl of RT buffer (50 mmol/l Tris-HCl (pH 8.3), 70 mmol/l KCl, 3 mmol/l MgCl$_2$, 10 mmol/l dithiothreitol) containing 600 U reverse transcriptase (Moloney murine leukemia virus reverse transcriptase, GIBCO-BRL), 500 mmol/l each deoxynucleotide triphosphate (dNTP, Pharmacia), 750 ng oligo dT primer set, and 40 U RNase inhibitor (Boehringer Mannheim). This mixture was incubated at 37° C. for 90 minutes, heated at 70° C. for 20 minutes, and stored at −20° C. until use.

PCR was performed on a DNA thermal cycler (Perkin Elmer-Cetus) in a round of cycles of denaturation at 94° C.×1 min., primer annealing at 64° C.×1 min. (β actin: 60° C.×1 min.), and chain elongation at 72° C.×1 min. to provide a PCR product (first round PCR).

When the densitometer unit (described below) of this PCR product was less than 500, a second round PCR with the nested inner primer set was carried out using a 2.5 μl aliquot of the first-round PCR product.

The PCR product thus obtained was assayed in accordance with the protocol given in the literature [J. Immunol., 147, 4307 (1991)], as follows.

Thus, the PCR product from 20 ng of total RNA was cloned on 1.3% agarose gel containing 0.05 μg/ml of ethidium bromide and photographed using polaroid film (Polaroid 665 film, Polaroid Corp.). The negative film was developed at 25° C. for 5 minutes and scanned with a densitomer (CS-9000, Shimadzu) to find the "densitomer unit". The result for the PCR product obtained in the absence of RNA under otherwise the same conditions was used as negative control. The primers used in the above procedures are shown in Table 3.

TABLE 3

| First round PCR primers | Base sequences |
| --- | --- |
| Outer sense primer | 5'-GGCATCTGAGACCAGTGAGAA-3' (SEQ ID NO:9) |
| Outer antisense primer | 5'-GAGAGTCAGACTTGAAAGCAGT-3' (SEQ ID NO:10) |
| Second round PCR primer | Base sequences |
| Inner sense primer | 5'-GCTGTCCCACTTACAGATGCA-3' (SEQ ID NO:11) |
| Inner antisense primer | 5'-TCAAAGCGCCAGCTGGAGTTT-3' (SEQ ID NO:12) |

As the primers for β actin used as an internal control, those described in the literature [Proc. Natl. Acad. Sci. USA., 82, 6133, (1985)] were used. The respective primers were invariably synthesized by the conventional chemical method.

To standardize the amount of RNA for RT-PCR and the difference in RNA decomposition of samples, the result (densitomer unit) with the WT1 gene was divided by the result with β actin and the product was used as the level of WT1 gene expression.

Furthermore, with the level of WT1 gene expression in the cell line K562 known to have the WT1 gene expressed [Lozzio, C. B. and Lozzio, B. B., Human chronic myelogenous leukemia cell line with positive Philadelphia chromosome, Blood, 45, 321–334 (1995)] as determined by the above procedure being taken as the reference (1.00), the levels of WT1 gene expression in various test fraction were calculated as relative ratios.

Figure 3:
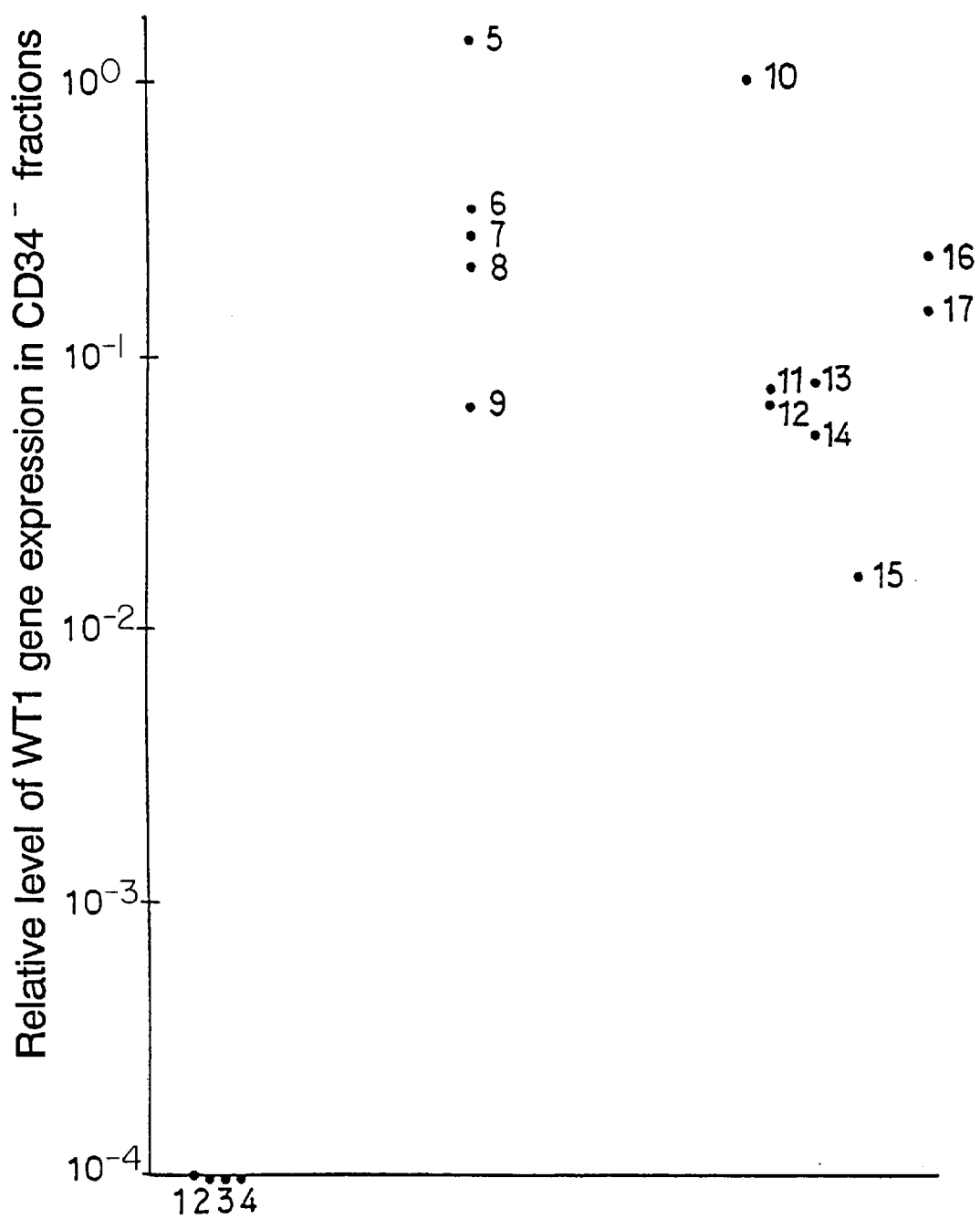
FIG. 3 is a diagrammatic representation of the data generated by determining the level of WT1 gene expression in various CD34⁻ cell fractions in accordance with Example 3.

The results are presented in FIG. 3.

Plotted on the ordinate are the relative levels of WT1 gene expression in various test cells (CD34$^-$ cell fractions) with the level of WT1 gene expression in K562 cell line (K562 in the table) being taken as 100°.

The cells tested were as follows.

(1)–(4) . . . The CD34$^-$ cell fraction of peripheral blood hematopoietic stem cells from patients
(5)–(9) . . . The CD34$^-$ cell fraction of leukemic cells
(10) . . . The CD34$^-$ cell fraction of gastric cancer cells
(11), (12) . . . The CD34$^-$ cell fraction of colon cancer cells
(13), (14) . . . The CD34$^-$ cell fraction of lung cancer cells
(15) . . . The CD34$^-$ cell fraction of breast cancer cells
(16), (17) . . . The CD34$^-$ cell fraction of ovary cancer cells The following can be understood from the diagram. Thus, fresh leukemic cells comprise CD34$^+$ and CD34$^-$ cells, both of which have the WT1 gene expressed at high levels [$10^{-1}$–$10^0$ level: see (5)–(9)]. On the other hand, the CD34$^-$ cell fractions of normal hematopoietic stem cells have the WT1 gene expressed at low levels, $\leq 10^{-4}$ [(1)–(4); however, the level of WT1 expression in those cells is high].

If the CD34$^-$ cell fraction of an isolated sample of hematopoietic stem cells contains leukemic cells (which are CD34$^-$), the WT1 level in those cells should have been elevated. Therefore, by determining the WT1 value of this CD34$^-$ cell fraction, leukemic cells can be detected provided that one leukemic cell is present among $10^3$–$10^4$ normal cells. When the presence of leukemic cells in the CD34$^-$ cell fraction of the hematopoietic cell sample is thus confirmed by the above detection, it is certain that the CD34$^+$ cell fraction of the hematopoietic stem cells in the graft material also contains leukemic cells, indicating that the use of such cells for transplantation should be avoided for safety.

Referring to solid cancer cells, which are intrinsically CD34$^-$, it is clear that if a sample of hematopoietic stem cells has been contaminated with cancer cells, most of them should be present in the CD34$^-$ cell fraction. Therefore, by determining the WT1 value of this fraction, the occurrence of cancer cells can be detected in the same manner.

Thus, in accordance with the technology of the present invention, the presence or absence of leukemic cells or cancer cells in a graft tissue material can be ascertained with certainty.

INDUSTRIAL APPLICABILITY

In accordance with the present invention there are provided a technology for detecting solid cancer cells and atypia and a technology for testing a graft material. Those technologies are of great clinical use because they permit detection and diagnosis of solid cancers and prediction of the risk of leukemic transformation or the prognosis of various diseases known to progress to leukemia, such as MDS, or confirmation of the safety of graft materials.

Particularly the technology for detecting solid cancer cells according to the invention is of use for elucidation of the etiologic mechanisms and pathology of various solid cancers and diagnosis of such diseases. More particularly, the present invention enables 1. the diagnosis of malignancy of a lesion,
2. the diagnosis of cancer cell invasion in the tissue including a primary lesion and cancer metastasis to remote organs inclusive of bone marrow or to lymph nodes,
3. the diagnosis of cancer cells in various body fluids, pleural fluid and ascites,
4. Detection of cancer cells in peripheral blood, and
5. Detection of cancer cells in the isolated bone marrow or peripheral blood stem cell fraction for bone marrow transplantation or peripheral blood stem cell transplantation.

Furthermore, the present inventors have so far gained evidence of the existence of high-expression type and low-expression type for the WT1 gene in various germ cell tumors and, therefore, the WT1 gene enables a new classification of malignancy of germ cell tumor and other solid cancers. Detection of such a difference in the property of solid cancers should provide a clinically useful marker of malignancy or the like particularly in germ cell tumors which cannot be pathologically differentiated.

What is claimed is:

1. A method for detecting solid cancer cells selected from the group consisting of gastric, colon, lung, breast, germ cell tumor and thyroid cancer cells, which comprises determining the level of expression of the WT1 gene in a test tissue to detect the solid cancer cells.

2. The method according to claim 1 wherein the level of expression of the WT1 gene is determined by detecting a transcript of said gene.

3. A method for testing a graft material tissue for the presence of leukemic and/or solid cancer cells comprising the steps of:

(A) obtaining graft material tissue useful for bone marrow transplantation or peripherial blood stem cell transplantation; and (B) detecting the level of expression of the WT1 gene in a CD34$^-$ cell fraction of said graft material tissue, so as to detect said leukemic and/or solid cancer cells.

4. A method for detecting atypia which comprises determining the level of expression of the WT1 gene in a test tissue to thereby detect atypia.

5. The method according to claim 4 wherein the test tissue is one from a patient with myelodysplastic syndrome.

6. The method according to claim 4 wherein the level of expression of the WT1 gene is determined by detecting a transcript of said gene.

7. The method according to claim 3 wherein the level of expression of the WT1 gene is determined by detecting a transcript of said gene.

* * * * *

SEQUENCE LISTING

<160> NUMBER OF SEQ ID NOS: 12

<210> SEQ ID NO: 1
<211> LENGTH: 21
<212> TYPE: DNA
<213> ORGANISM: synthetic construct

<400> SEQUENCE: 1
ggcatctgag accagtgaga a                                                 21

<210> SEQ ID NO: 2
<211> LENGTH: 22
<212> TYPE: DNA
<213> ORGANISM: synthetic construct

<400> SEQUENCE: 2

-continued gagagtcaga cttgaaagca gt 22

<210> SEQ ID NO: 3
<211> LENGTH: 21
<212> TYPE: DNA
<213> ORGANISM: synthetic construct

<400> SEQUENCE: 3
gctgtcccac ttacagatgc a 21

<210> SEQ ID NO: 4
<211> LENGTH: 21
<212> TYPE: DNA
<213> ORGANISM: synthetic construct

<400> SEQUENCE: 4
tcaaagcgcc agctggagtt t 21

<210> SEQ ID NO: 5
<211> LENGTH: 21
<212> TYPE: DNA
<213> ORGANISM: synthetic construct

<400> SEQUENCE: 5
ggcatctgag accagtgaga a 21

<210> SEQ ID NO: 6
<211> LENGTH: 22
<212> TYPE: DNA
<213> ORGANISM: synthetic construct

<400> SEQUENCE: 6
gagagtcaga cttgaaagca gt 22

<210> SEQ ID NO: 7
<211> LENGTH: 21
<212> TYPE: DNA
<213> ORGANISM: synthetic construct

<400> SEQUENCE: 7
gctgtcccac ttacagatgc a 21

<210> SEQ ID NO: 8
<211> LENGTH: 21
<212> TYPE: DNA
<213> ORGANISM: synthetic construct

<400> SEQUENCE: 8
tcaaagcgcc agctggagtt t 21

<210> SEQ ID NO: 9
<211> LENGTH: 21
<212> TYPE: DNA
<213> ORGANISM: synthetic construct

<400> SEQUENCE: 9
ggcatctgag accagtgaga a 21

<210> SEQ ID NO: 10
<211> LENGTH: 22
<212> TYPE: DNA
<213> ORGANISM: synthetic construct

<400> SEQUENCE: 10

```
gagagtcaga cttgaaagca gt                                      22

<210> SEQ ID NO: 11
<211> LENGTH: 21
<212> TYPE: DNA
<213> ORGANISM: synthetic construct

<400> SEQUENCE: 11
gctgtcccac ttacagatgc a                                       21

<210> SEQ ID NO: 12
<211> LENGTH: 21
<212> TYPE: DNA
<213> ORGANISM: synthetic construct

<400> SEQUENCE: 12
tcaaagcgcc agctggagtt t                                       21
```